United States Patent [19]

Scardera et al.

[11] 4,160,776
[45] Jul. 10, 1979

[54] ALKOXY-BIS (TRIALKOXYSILOXY)-SILANE SURFACTANTS

[75] Inventors: Michael Scardera, Hamden; David F. Gavin, Cheshire, both of Conn.

[73] Assignee: Olin Corporation, New Haven, Conn.

[21] Appl. No.: 920,579

[22] Filed: Jun. 29, 1978

[51] Int. Cl.² ............................................. C07F 7/18
[52] U.S. Cl. .............................................. 260/448.8 R
[58] Field of Search .................................. 260/448.8 R

[56] References Cited

U.S. PATENT DOCUMENTS

| | | | |
|---|---|---|---|
| 2,990,377 | 6/1961 | May | 260/448.8 R X |
| 3,509,192 | 4/1970 | Niederprüm et al. | 260/448.8 R |
| 3,803,197 | 4/1974 | Anderson et al. | 260/448.8 R UX |
| 3,960,913 | 6/1976 | Knollmueller | 260/448.8 R |
| 3,965,135 | 6/1976 | Knollmueller | 260/448.8 R X |
| 3,965,136 | 6/1976 | Knollmueller | 260/448.8 R X |
| 3,994,948 | 11/1976 | Jayne et al. | 260/448.8 R |
| 4,051,053 | 9/1977 | Elliot et al. | 260/448.8 R X |
| 4,058,546 | 11/1977 | Knollmueller | 260/448.8 R |
| 4,077,993 | 3/1978 | Knollmueller | 260/448.8 R |

OTHER PUBLICATIONS

Prior art cited in Paper #2.

*Primary Examiner*—Paul F. Shaver
*Attorney, Agent, or Firm*—Robert J. Feltovic; Thomas P. O'Day

[57] ABSTRACT

Novel surface active agents are disclosed having the formula:

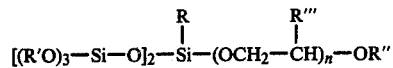

wherein R is hydrogen, an alkyl, alkenyl, aryl or aralkyl group; each R' is independently selected from the same group as R with the proviso that at least a majority of R' radicals attached to each Si atom are sterically hindered alkyl groups having at least 3 carbon atoms; R" is alkyl or alkenyl of 1–20 carbons; R'" is hydrogen or methyl; and n is an integer of from about 5 to about 50.

17 Claims, No Drawings

ALKOXY-BIS (TRIALKOXYSILOXY)-SILANE SURFACTANTS

A novel silicate-based surface active agent has now been found, according to the present invention, which features the general formula:

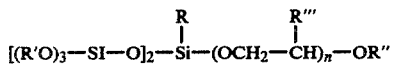
$$[(R'O)_3-Si-O]_2-Si-(OCH_2-CH)_n-OR'' \qquad I$$

wherein R is hydrogen, an alkyl, alkenyl, aryl or aralkyl; each R' is independently selected from the same group as R with the proviso that at least a majority of R' radicals attached to each Si atom are sterically hindered alkyl groups having at least 3 carbon atoms; R" is alkyl or alkenyl of 1-20 carbon atoms; each R''' is hydrogen or methyl; and n is an integer from about 5 to about 50.

Desirably, R is hydrogen, an alkyl or alkenyl having about 1 to about 18 carbon atoms or an aryl or aralkyl having about 6 to about 24 carbon atoms. Preferably, R is hydrogen, an alkyl having about 1 to about 8 carbon atoms or an aryl or aralkyl having about 6 to about 14 carbon atoms. In Formula I, each R' is independently selected from the same group as R, with the proviso that at least a majority of the R' radicals attached to each Si atom are sterically hindered alkyl groups having at least 3 carbon atoms. Preferably, all of the R' groups are these sterically hindered alkyl groups. The desired and preferred groups for R' are the same as for R, subject to the preceding proviso. Desirably, at least a majority of the R' radicals are sterically hindered alkyl groups having about 3 to about 24 carbon atoms and preferably are sterically hindered alkyl groups having about 4 to about 12 carbon atoms. By sterically hindered alkyl groups is meant alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly useful sterically hindered alkyl groups include sec. butyl, isobutyl, 2-ethyl butyl, 2-ethyl pentyl, 3-ethyl pentyl, 2-ethyl hexyl, 3-ethyl hexyl, 2,4-dimethyl-3-pentyl, etc. Sec. butyl is most preferred. R" preferably is an alkyl radical having 1 to about 12 carbon atoms, such as methyl, ethyl, propyl, butyl, pentyl, hexyl, etc. Lower alkyl is particularly preferred. Methyl is most preferred. The integer n preferably ranges from about 10 to about 30; most preferably it ranges from about 15 to about 30. Each R''' is independently selected from hydrogen or methyl. Preferably, in about 0 to about 80 percent by weight of the groups

$$-(OCH_2-CH)-,$$

R''' is methyl; more preferably in about 0 to about 50 percent of the groups, R''' is methyl. In a particularly preferred embodiment, in all of the groups, R''' is hydrogen.

A preferred formula for the surfactant composition of the present invention is:

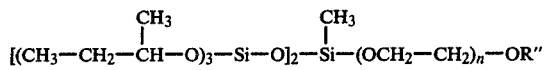
$$[(CH_3-CH_2-CH-O)_3-Si-O]_2-Si-(OCH_2-CH_2)_n-OR''$$
with $CH_3$ substituents as shown wherein n and R" are as defined above.

In a preferred method for preparing the novel silicate-based surfactants of the present invention, a polyalkoxylated linear aliphatic alcohol is reacted with a bis(trialkoxysiloxy) alkylhalosilane.

The polyalkoxylated alcohol used in the method of the present invention has the formula:

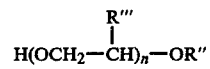
$$H(OCH_2-CH)_n-OR'' \qquad II$$

wherein R", R''' and n are as defined above in Formula I. This compound can be prepared by common oxyalkylation techniques. For example, it can be prepared by condensing, in the presence of an alkaline catalyst, such as KOH, a linear aliphatic alcohol, with ethylene oxide, or ethylene oxide and propylene oxide, in random or block arrangement. Portions of propylene oxide in the alkoxylation mixture may range from 0 to 80 percent by weight, preferably from 0-50 percent by weight. A particularly preferred embodiment features 100 percent ethylene oxide.

The polyalkoxylated alcohol of Formula II above is reacted with a bis(trialkoxysiloxy) alkylhalosilane of the formula:

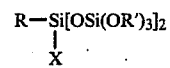
$$R-Si[OSi(OR')_3]_2 \qquad III$$
with X substituent wherein R and R' are as defined above in Formula I, and X is a halogen selected from F, Cl, Br and I. Preferably, X is Cl, Br or I; Cl is most preferred.

The compounds of Formula III are disclosed in commonly assigned U.S. Pat. No. 3,965,136 (Knollmueller) and a method for their preparation is described therein. The disclosure of this patent is hereby incorporated in its entirety by reference.

In a preferred method of preparation, the polyalkoxylated alcohol compound and the bis(trialkoxysiloxy) alkylhalosilane compound are reacted in the presence of a hydrogen halide acceptor base compound. The acceptor may be any compound which will accept hydrogen halide and thereby promote the formation of the surfactant compounds of the present invention pursuant to Equation A shown below. Among the preferred acceptors are the nitrogenated tertiary organic base compounds having at least 3 carbon atoms, e.g., the lower alkyl and aryl tertiary amines such as triethylamine, tributylamine, as well as pyridine, substituted pyridine, N,N'-dimethylaniline, etc. Alternatively, commonly used phase transfer catalysis methods for working in aqueous/non-polar solvent systems may also be employed.

The formation of the novel surfactant compounds of the present invention using the above reactants may be represented by the following equation:

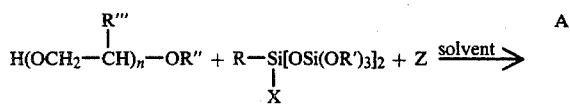
$$H(OCH_2-CH)_n-OR'' + R-Si[OSi(OR')_3]_2 + Z \xrightarrow{solvent} \qquad A$$
with R''' and X substituents -continued

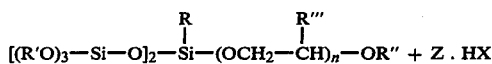

wherein Z is the hydrogen halide acceptor base and the other reactants are described above.

Equation A suggests that the principal reaction in the method of preparing the surfactant compounds of the present invention be carried out in a solvent. While the solvent is not necessary, it does serve to moderate the rate of reaction and thereby to enhance the separation of the acceptor-hydrogen halide Z.HX from the surfactant compound product. The solvent used may be any non-protonic solvent which dissolves the reactants and does not interfere with the Equation A reaction. Among the solvents which may be used are benzene, toluene, xylene, high boiling petroleum ether, other ethers such as tetrahydrofuran, and the like.

In general, a stoichiometric amount of the reactants are used. The total solvent employed in the reaction is a matter of choice and is not critical to the reaction. The hydrogen halide acceptor base also is advantageously used in a stoichiometric amount, based on the amount of bis(trialkoxysiloxy) alkylhalo-silane used.

The reaction represented by Equation A may be performed at very low temperatures, room temperature, or even very high temperatures as long as there is no detrimental effect on the reactants or products. Thus, the reaction may be carried out at −30° C. up to the reflux temperature of the lowest boiling constituent, and it is preferably carried out at about 0° C. to about 100° C. In a preferred method, the reaction is started at ambient temperature, and is completed at a higher temperature to drive the reaction as far as possible to completion. In any event, the surfactant compounds are separated from the product mixture by filtrations, distillations or other conventional separation techniques, and the particular separation system chosen merely depends upon the desired purity of the final product and its ultimate utility.

The surfactant products of this invention may be used in a variety of applications, such as in detergent formulations, or as emulsifying agents. Also, they may be utilized in non-aqueous surfactant applications, such as in urethane foam formulations. These novel silicate-based surface active agents are unlike conventional silicate surfactants in that they exhibit favorable hydrolytic stability due to the shielding of the silicon atoms with the sterically hindered constituents, as described. The invented surfactants function similar to a silicone in reducing surface tension, and further feature the advantage of exhibiting oil or water solubility, depending on the particular hydrophilic moiety employed in formulating the surfactant composition.

The following examples depict preparation of the novel surfactant composition of the present invention as well as the favorable surfactant properties demonstrated thereby. The examples are intended to be illustrative and not limiting in nature.

EXAMPLE 1

Preparation of Polyethylene Glycol Mono-Methyl Ether

A 500 ml round bottom flask containing a magnetic stirring bar was fitted with a thermometer, graduated dropping funnel, nitrogen purge and dry ice condenser. The flask contained 24 g (0.2 mole) diethylene glycol mono-methyl ether and 0.2 g potassium hydroxide as catalyst. Under a nitrogen atmosphere, ethylene oxide, 160 g (3.6 moles), was added dropwise via the dropping funnel to the glycol ether at 140–165° C. with stirring. Upon completion of the ethylene oxide addition, the reaction product was cooled and weighed-product weight 184 g (glycol ether-ethylene oxide ratio was 1:18, methyl-ethylene oxide ratio was 1:20, molecular weight was 912).

EXAMPLE 2

Preparation of Methoxy-Ethoxy-Bis(Tributoxysiloxy) Methylsilane

In a 3-necked round bottom flask containing a magnetic stirring bar was placed 30.4 g (0.033 mole) glycol ether-ethylene oxide product from Example 1, 2.8 g (0.035 mole) pyridine and 50 g toluene. The flask was fitted with a thermometer, dropping funnel, and an air condenser. Bis(tributoxysiloxy)-methylchlorosilane, 20.1 g (0.033 mole) and 50 g toluene were mixed, placed in the dropping funnel, and gradually added to the contents of the flask with stirring at ambient temperature. Upon reaction, the white pyridine-HCl salt formed. Addition was complete in one hour, the temperature raised to 70° C. and heated an additional two hours to insure complete reaction. The reaction mixture was cooled to ambient temperature, the salt filtered off, and the clear filtrate placed on a rotary evaporator and heated to 70° C. under water aspirator vacuum for seven hours to insure removal of the excess pyridine and toluene solvent. The product was cooled and weighed. Product weight of the bis(tributoxysiloxy)-methylsilane-ethoxy-methyl adduct was 47.3 g (theory 48.8 g, yield 97%).

EXAMPLES 3, 4 AND 5

Additional methoxy-ethoxy-bis(tributoxysiloxy)-methylsilane surfactants were prepared using a procedure similar to that described in Example 2. The reactant and product specifications are set forth in Table I below.

TABLE I

| | EXAMPLES | | |
|---|---|---|---|
| | 3 | 4 | 5 |
| Reactants | | | |
| Glycol-EO Adduct | | | |
| $CH_3$—EO Ratio | 1:15 | 1:25 | 1:30 |
| Molecular Weight | 692 | 1132 | 1352 |
| Weight (g) | 35 | 22.6 | 27 |
| Moles | 0.05 | 0.02 | 0.02 |
| Pyridine | | | |
| Weight (g) | 4.3 | 1.7 | 1.7 |
| Moles | 0.054 | 0.022 | 0.022 |
| Bis(Tributoxysiloxy)- Methylchlorosilane | | | |
| Weight (g) | 30 | 12 | 12 |
| Moles | 0.05 | 0.02 | 0.02 |
| Product | | | |
| Weight (g) | 58.7 | 33.5 | 38.4 |
| Theory (g) | 62.9 | 34.0 | 38.4 |
| Percent Yield | 93.3 | 98.5 | 100 |

Surface properties of the products of Examples 2-5 are shown in Table II. The methods for determining each of the properties listed are as follows:

Cloud Point—ASTM Designation D 2024-65

Surface and Interfacial Tension—ASTM Designation D 1331-56

Draves Wetting Times—ASTM Designation D 2281-68

Ross-Miles Foam Heights—ASTM Designation D 1173-53

These surfactants indicated excellent water solution stability over a 12-day period. Surfactants prepared with a polyisopropylsilicate hydrophobe hydrolyzed within 24 hours. Surface tension measurements after standing for 40 days also exhibited good to excellent stability as follows:

|  | Surface Tension, dynes/cm, 0.001% Solution | |
|---|---|---|
|  | Initial | After 40 Days |
| Example 2 | 32 | 34 |
| Example 3 | 34 | 43 |
| Example 4 | 31 | 44 |
| Example 5 | 35 | 44 |

TABLE II

|  | EXAMPLES | | | |
|---|---|---|---|---|
| Sample # | 2 | 3 | 4 | 5 |
| Moles EO (m) | 20 | 15 | 25 | 30 |
| Cloud Point, 1%, °C. | 65 | <0 | 72 | 80 |
| Surface Tension dynes/cm* | | | | |
| 0.1% | 23 | 24 | 25 | 26 |
| 0.01 | 24 | 24 | 26 | 27 |
| 0.001 | 32 | 34 | 31 | 35 |
| Interfacial Tension, dynes/cm (vs mineral oil) | | | | |
| 0.1% | 2 | 3 | 4 | 5 |
| 0.01 | 4 | 5 | 5 | 6 |
| 0.001 | 11 | 15 | 10 | 14 |
| Draves Wetting Times, secs. | | | | |
| at 25° C. 0.25 | 24 | 170 | 37 | 54 |
| 0.1 | 59 | >180 | 84 | 130 |
| at 60° C. 0.25 | 48 | >180 | 31 | 30 |
| 0.1 | 76 | >180 | 58 | 77 |
| Ross-Miles Foam, Height, mm 10 (initial/after 5 min.) | | | | |
| at 25° C. 0.25% | 55/50 | 15/15 | 100/90 | 85/75 |

*For comparison, the Surface Tension of distilled water is approximately 72 dynes/cm.

We claim:

1. A surfactant composition having the formula:

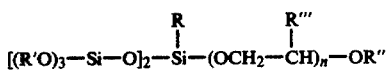

wherein n is an integer of about 5 to about 50; R is selected from hydrogen, alkyl, alkenyl, aryl, and aralkyl; R' is independently selected from the same group as R with the proviso that at least a majority of the R' groups on each Si atom are sterically hindered alkyl groups having at least 3 carbon atoms; R" is alkyl or alkenyl having about 1 to about 20 carbon atoms; and each R''' is independently selected from hydrogen and methyl.

2. The surfactant composition of claim 1 wherein R is hydrogen, an alkyl or alkenyl having about 1 to about 18 carbon atoms or an aryl or aralkyl having about 6 to about 24 carbon atoms and wherein each R' is independently selected from the same group as R, subject to the above proviso.

3. The surfactant composition of claim 2 wherein a majority of the R' radicals are sterically hindered alkyl groups having about 3 to about 24 carbon atoms.

4. The surfactant composition of claim 1 wherein R is hydrogen, an alkyl having about 1 to about 8 carbon atoms or an aryl or aralkyl having about 6 to about 14 carbon atoms and wherein each R' is independently selected from the same group as R, subject to the above proviso.

5. The surfactant composition of claim 4 wherein the R' radicals are sterically hindered alkyl groups having about 4 to about 12 carbon atoms.

6. The surfactant composition of claim 1 wherein R is methyl and R' is sec. butyl.

7. The surfactant composition of claim 1 wherein R" is alkyl of about 1 to about 12 carbon atoms.

8. The surfactant composition of claim 7 wherein R" is lower alkyl of about 1 to about 4 carbon atoms.

9. The surfactant composition of claim 8 wherein R" is methyl.

10. The surfactant composition of claim 1 wherein n ranges from about 10 to about 30.

11. The surfactant composition of claim 10 wherein n ranges from about 15 to about 30.

12. The surfactant composition of claim 1 wherein R''' is methyl in 0 to about 80 percent by weight of the alkoxy groups

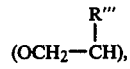

and the resulting propoxy and ethoxy groups are positioned in random or block arrangement.

13. The surfactant composition of claim 12 wherein R''' is methyl in 0 to about 50 percent of the alkoxy groups.

14. The surfactant composition of claim 13 wherein R''' is hydrogen in all of the alkoxy groups.

15. The surfactant composition of claim 1 having the formula:

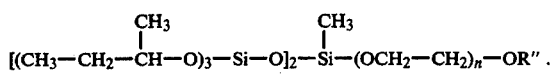

16. The surfactant composition of claim 15 wherein n is an integer from about 10 to about 30, and R" is alkyl of about 1 to about 12 carbon atoms.

17. The surfactant composition of claim 16 wherein n is an integer from about 15 to about 30, and R" is methyl.